(12) United States Patent
Guerra

(10) Patent No.: US 7,909,822 B2
(45) Date of Patent: *Mar. 22, 2011

(54) BIPOLAR TISSUE DEBRIDER AND METHOD

(75) Inventor: Paul Guerra, Boulder, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/714,970

(22) Filed: Mar. 1, 2010

(65) Prior Publication Data

US 2010/0160912 A1    Jun. 24, 2010

Related U.S. Application Data

(63) Continuation of application No. 11/635,754, filed on Dec. 7, 2006, now Pat. No. 7,682,360.

(51) Int. Cl.
*A61B 18/18* (2006.01)

(52) U.S. Cl. ............ 606/48; 606/49; 606/167; 606/170; 606/171; 606/177; 606/180

(58) Field of Classification Search ............ 606/41, 606/45, 48, 50, 167, 169, 170, 171, 176, 606/178, 179
See application file for complete search history.

(56) References Cited

U.S. PATENT DOCUMENTS

| | | | |
|---|---|---|---|
| 4,276,880 A | 7/1981 | Malmin | |
| 4,505,679 A | 3/1985 | Gutentag | |
| 4,778,679 A | 10/1988 | Silvetti | |
| 4,846,181 A | 7/1989 | Miller | |
| 5,007,895 A | 4/1991 | Burnett | |
| 5,200,430 A | 4/1993 | Federman | |
| 5,324,300 A * | 6/1994 | Elias et al. | 606/180 |
| 5,540,695 A | 7/1996 | Levy | |
| 5,588,167 A | 12/1996 | Pahno et al. | |
| D381,747 S | 7/1997 | Kapec et al. | |
| 5,648,141 A | 7/1997 | Butterworth et al. | |
| 5,685,838 A | 11/1997 | Peters et al. | |
| 5,735,934 A | 4/1998 | Spears | |
| 5,782,795 A | 7/1998 | Bays | |
| 5,843,052 A | 12/1998 | Benja-Athon | |
| 5,957,881 A | 9/1999 | Peters et al. | |
| 6,043,407 A | 3/2000 | Lodhi et al. | |
| 6,183,433 B1 | 2/2001 | Bays | |
| 6,293,957 B1 | 9/2001 | Peters et al. | |
| 6,336,926 B1 | 1/2002 | Goble | |
| 6,371,934 B1 | 4/2002 | Jackson et al. | |
| 6,375,635 B1 | 4/2002 | Moutafis et al. | |
| 6,387,095 B1 | 5/2002 | Kennett et al. | |
| 6,394,996 B1 | 5/2002 | Lawrence et al. | |
| 6,451,017 B1 | 9/2002 | Moutafis et al. | |
| 6,511,493 B1 | 1/2003 | Moutafis et al. | |

(Continued)

*Primary Examiner* — Linda C Dvorak
*Assistant Examiner* — Amanda Scott

(57) ABSTRACT

A debrider apparatus is disclosed. The debrider includes a first tubular member that is adapted to connect to a first potential of an electrosurgical generator. A second tubular member is at least partially disposed within the first tubular member and is adapted to connect to a second potential of the electrosurgical generator. At least one tubular member is selectively movable relative to the other. A first set of teeth is disposed around at least a portion of a distal periphery of the first tubular member. A second set of teeth is disposed around at least a portion of a distal periphery of the second tubular member. At least one switch is operably coupled to at least one of the tubular members and activates movement of one tubular member and supplies respective electrical potentials to the tubular members.

4 Claims, 3 Drawing Sheets

U.S. PATENT DOCUMENTS

| | | | |
|---|---|---|---|
| 6,562,013 B1 | 5/2003 | Marasco, Jr. | |
| 6,575,978 B2 | 6/2003 | Peterson et al. | |
| 6,629,974 B2 | 10/2003 | Penny et al. | |
| 6,645,510 B1 | 11/2003 | Coury et al. | |
| 6,669,710 B2 | 12/2003 | Moutafis et al. | |
| 6,716,184 B2 | 4/2004 | Vaezy et al. | |
| 6,723,091 B2 | 4/2004 | Goble et al. | |
| 6,755,196 B2 | 6/2004 | Musso et al. | |
| 6,786,897 B2 | 9/2004 | Mc Ie et al. | |
| 6,837,907 B2 | 1/2005 | Wolfinbarger, Jr. et al. | |
| 6,851,430 B2 | 2/2005 | Tsou | |
| 6,869,412 B2 | 3/2005 | Ross | |
| 6,878,142 B2 | 4/2005 | Lawrence et al. | |
| 6,899,712 B2 | 5/2005 | Moutafis et al. | |
| 6,923,792 B2 | 8/2005 | Staid et al. | |
| 6,923,803 B2 | 8/2005 | Goble | |
| 6,960,182 B2 | 11/2005 | Moutafis et al. | |
| 7,001,380 B2 | 2/2006 | Goble | |
| 7,070,574 B2 | 7/2006 | Jackson et al. | |
| 7,179,225 B2 | 2/2007 | Shluzas et al. | |
| 7,195,617 B2 | 3/2007 | Papendick et al. | |
| 7,226,451 B2 | 6/2007 | Shluzas et al. | |
| 7,232,456 B2 | 6/2007 | Chernoff | |
| 7,247,161 B2 | 7/2007 | Johnston et al. | |
| 7,278,994 B2 | 10/2007 | Goble | |
| 7,300,436 B2 | 11/2007 | Penny et al. | |
| 2003/0060862 A1 * | 3/2003 | Goble et al. | 607/96 |

* cited by examiner

BIPOLAR TISSUE DEBRIDER AND METHOD

CROSS-REFERENCE TO RELATED APPLICATIONS

This application is a continuation of U.S. patent application Ser. No. 11/635,754 filed on Dec. 7, 2006, now U.S. Pat. No. 7,682,360,, the entire contents of which are incorporated herein by reference.

BACKGROUND

1,. Technical Field

The present disclosure relates to the field of tissue debriders. More particularly, the present disclosure relates to a tissue debrider that shears and cauterizes tissue and a method of using the same.

2,. Description of Related Art

Debriders are generally used by physicians to cut tissue at a tissue treatment site, e.g., during sinus or arthritis surgery. Generally, these surgical instruments utilize a cutting tube mounted within an outer cutting housing. The cutting tube is hollow and may be connected to a source of suction. The cutting tubes either rotate or reciprocate within the outer tube housing to cut tissue that is located between the two tubes. The suction source is used to remove debris, e.g., the sheared tissue, from the tissue treatment site.

After such a surgical treatment is utilized, bleeding may occur from the surgical site and it is often desirable to cauterize or coagulate tissue that has been cut. Debriders that are used in the prior art do not have the capability to coagulate or cauterize tissue. Accordingly, a separate coagulation or cautery tool is subsequently used to coagulate the tissue.

SUMMARY

The present disclosure combines the benefits of a conventional debrider and an electrosurgical instrument, such as a coagulator. As such, the apparatus and method of the present disclosure include using a single instrument, i.e., a debrider apparatus, to both shear and cauterize/coagulate tissue.

The present disclosure relates to a debrider apparatus. The debrider apparatus includes a first tubular member, a second tubular member, a first set of teeth, a second set of teeth and at least one switch. The first tubular member includes a distal portion and is adapted to connect to a first potential of an electrosurgical generator (e.g., an active electrode). The second tubular member includes a distal portion, is at least partially disposed within the first tubular member and is adapted to be connected to a second potential of the electrosurgical generator (e.g., a return electrode). At least one of the first and the second tubular member is selectively movable (e.g., rotationally or reciprocably) relative to the other. The first set of teeth is disposed around at least a portion of a periphery of the first tubular member and is adjacent its distal portion. The second set of teeth is disposed around at least a portion of a periphery of the second tubular member and is adjacent its distal portion. The at least one switch is operably coupled to at least one of the first and second tubular members and both activates movement of one of the tubular members relative to the other tubular member and supplies respective electrical potential to the first and second tubular members.

In a disclosed embodiment, the debrider apparatus includes two switches. One of the two switches is configured to activate movement of the tubular members relative to one another and the other switch is configured to supply respective electrical potentials to the first and second tubular members.

In a disclosed embodiment, about 25% to about 75% of the periphery of the first tubular member includes teeth and the remaining portion defines a non-cutting zone. In another embodiment, a distal surface of the first and second tubular members is beveled at an angle relative to a longitudinal axis defined by the first tubular member.

An embodiment of the present disclosure also includes at least one lumen defined within at least one of the tubular members. The lumen is configured to remove material from a tissue treatment site. In a disclosed embodiment, the lumen is configured to supply a solution to the tissue treatment site.

The present disclosure also relates to a method of using a single instrument to shear and cauterize tissue. This method includes providing a debrider apparatus, such as a debrider apparatus described above, placing the debrider apparatus adjacent a tissue treatment area, and activating the at least one switch to both rotate one of the first and second tubular members relative to one another and to simultaneously provide electrical energy to the first and second tubular members.

The present disclosure also relates to a system for shearing and electrosurgically treating tissue. The system includes a debrider apparatus, such as a debrider apparatus described above, and an electrosurgical generator that supplies the first tubular member with a first electrical potential and supplies the second tubular member with a second electrical potential.

DESCRIPTION OF THE DRAWINGS

Various embodiments of the presently disclosed surgical instrument are disclosed herein with reference to the drawings, wherein.

DETAILED DESCRIPTION

Figure 1:
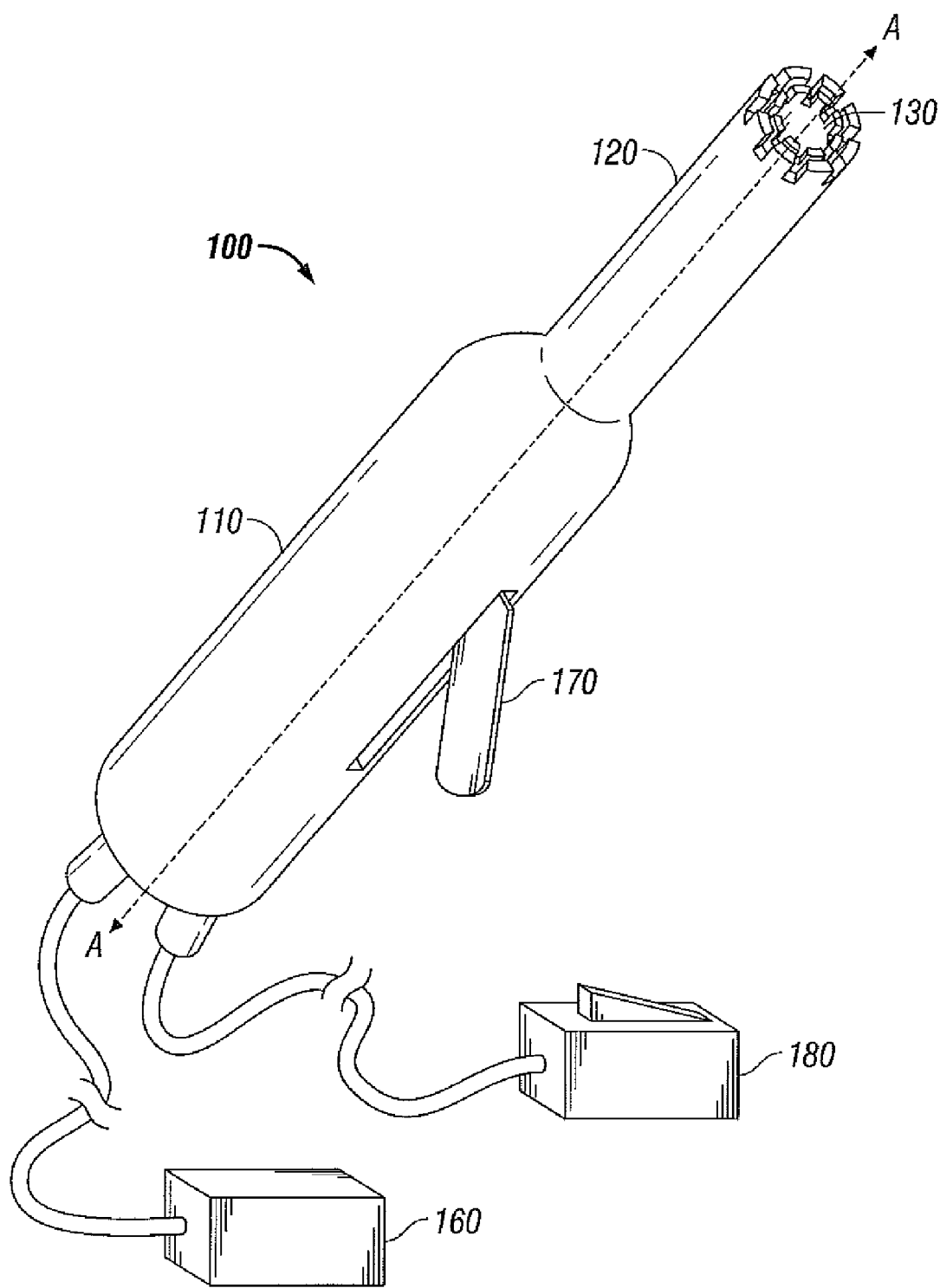
FIG. 1 is a perspective view of a debrider apparatus according to an embodiment of the present disclosure.
Figure 2:
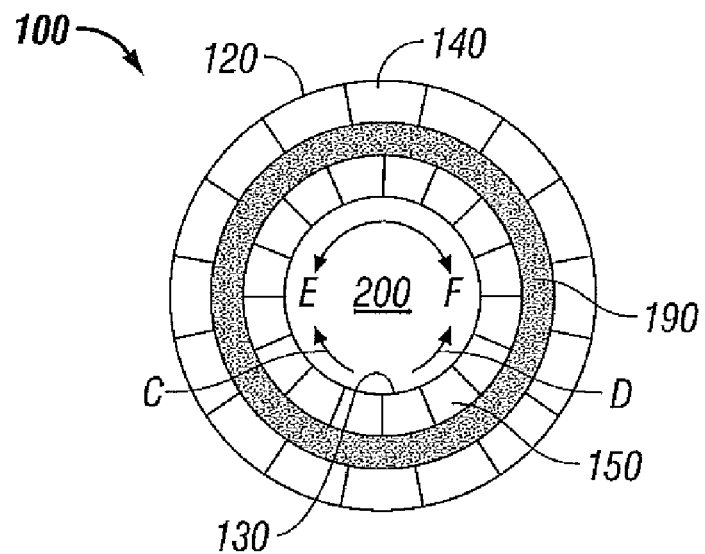
FIG. 2 is a top view of the debrider apparatus of FIG. 1.

Embodiments of the presently disclosed debrider apparatus are described in detail with reference to the drawings, in which like reference numerals designate identical or corresponding elements in each of the several views. As is common in the art, the term "proximal" refers to that part or component closer to the user or operator, e.g., surgeon or physician, while the term "distal" refers to that part or component farther away from the user.

Referring to FIG. 1, an embodiment of a debrider apparatus 100 of the present disclosure is illustrated. Debrider apparatus 100 of this embodiment includes a body portion 110, a first tubular member 120, and a second tubular member 130. As illustrated in FIGS. 2-5, second tubular member 130 is at least partially disposed within first tubular member 120. Additionally, second tubular member 130 may be moved (e.g., rotated in the direction of arrow C or arrow D or reciprocated back and forth in the direction of double-head arrow E-F, see FIG. 2) with respect to first tubular member 120.

First tubular member 120 defines a first axis A-A extending therethrough and includes a first set of teeth 140 disposed at least partially around a distal portion thereof. Second tubular member 130 includes a second set of teeth 150 disposed at least partially around a distal portion thereof. Upon movement of second tubular member 130, tissue from a tissue treatment area is sheared. Specifically, in one embodiment, tissue on the tissue treatment area that is located between first set of teeth 140 and second set of teeth 150 is sheared from rotational movement of second set of teeth 150.

In addition to having the ability to shear tissue, debrider apparatus 100 of the present disclosure also cauterizes or coagulates tissue. Specifically, first tubular member 120 is charged with a first electrical potential, e.g., a positive charge or active electrode and second tubular member 130 is charged with a second electrical potential, e.g., a negative charge or return electrode. The first electrical potential is different from the second electrical potential, thus creating a potential difference therebetween. Thus, tissue on the tissue treatment area that is located between first set of teeth 140 and second set of teeth 150 is cauterized or coagulated during activation due to the potential difference between first tubular member 120 and second tubular member 130.

In the embodiment illustrated in FIG. 1, debrider apparatus 100 includes a power supply 160 (e.g., an electrosurgical generator), a hand switch 170 and a foot switch 180. While illustrated with each of these features, it is envisioned and within the scope of the present disclosure that debrider apparatus 100 may not include one or more of these features or may include additional features. Power supply 160 is configured to provide power to debrider apparatus 100. More specifically, power supply 160 may enable inner tubular member 130 to move (e.g., rotate or reciprocate), via a suitable motor (not explicitly shown in this embodiment), for example. Additionally, power supply 160 may be in the form of a battery that is contained at least partially within body portion 110 of debrider apparatus 100.

Hand switch 170 and/or foot switch 180 enables a user to control the speed (e.g., speed of rotation or reciprocation) of second tubular member 130 and the amount of electrical potential of first tubular member 120 and second tubular member 130, in a disclosed embodiment. For example, depressing hand switch 170 may control the movement of second tubular member 130 and depressing foot switch 180 may control the power supplied to the first tubular member 120 and the second tubular member 130. It is also envisioned that hand switch 170 or foot switch 180 may operate to control both the speed and the power. Additionally, it is envisioned that at least one more switch (not explicitly shown in the illustrated embodiment) is provided to control irrigation and/or removal of material through at least one lumen, as discussed below. It is also envisioned that a single switch (e.g., hand switch 170 or foot switch 180) is able to control more than one of these functions.

In the embodiment illustrated in FIGS. 2-5, an insulation layer 190 is disposed between first tubular member 120 and second tubular member 130. Insulation layer 190, such as an insulative sheath, coating, or bearing, allows for differences in electrical potential between first tubular member 120 and second tubular member 130 to exist while preventing a "short" therebetween. Insulation layer 190 may be made from any suitable insulative material, such as synthetic resinous fluorine-containing polymers sold under the trademark TEFLON®, for example.

With continued referenced to FIGS. 2-5, a lumen 200 is defined within second tubular member 130 and extends the length thereof. In the illustrated embodiments, lumen 200 is disposed through the center of second tubular member 130 and may be configured to extend from a part of body portion 110 to a distal portion of first tubular member 120 or second tubular member 130. In use, lumen 200 may be used for suction and/or irrigation. Specifically, when used for suction, lumen 200 may remove debris (e.g., sheared tissue) from the operating field or tissue treatment area. In this embodiment, suction through lumen 200 may be activated as movement of second tubular member 130 begins and/or as power is being supplied to debrider apparatus 100. When used for irrigation, lumen 200 may provide the operating field or tissue treatment area with an amount of cleaning or sanitizing solution, such as saline. In the embodiment illustrated in FIG. 4, secondary lumens 202, 204 are illustrated between first tubular member 120 and second tubular member 130 (shown within insulation layer 190). Here, lumen 200 may be used for suction and secondary lumens 202, 204 may be used for irrigation, or vice versa. It is envisioned that at least one secondary lumen 202, 204 extends to a portion of debrider apparatus 100 that is located proximally of first set of teeth 140.

Figure 3:
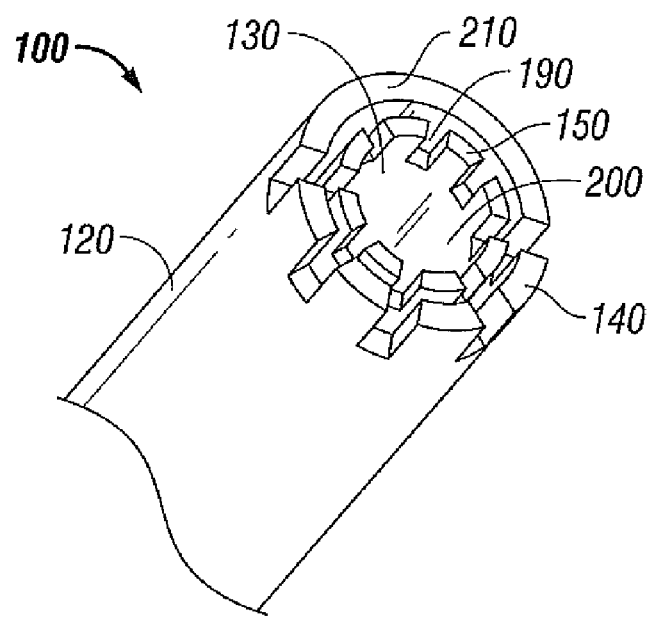
FIG. 3 is a perspective view of a distal portion of a debrider apparatus according to an embodiment of the present disclosure.
Figure 4:
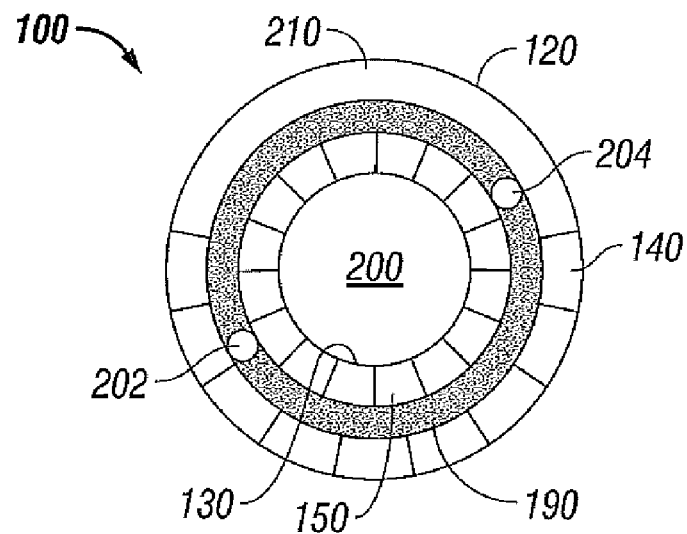
FIG. 4 is a top view of the debrider apparatus of FIG. 3.

Referring to FIGS. 3 and 4, first tubular member 120 of debrider apparatus 100 is illustrated having a non-cutting zone 210. Non-cutting zone 210 is a portion of the distal periphery of first tubular member 120 that contains no teeth from first set of teeth 140. That is, first set of teeth 140 do not extend around the entire periphery of a distal portion of first tubular member 120. Non-cutting zone 210 may incorporate a reasonable percentage of the periphery of first tubular member 120, such as between about 25% to about 75%. In use, the tissue located between non-cutting zone 210 and second set of teeth 150 is not sheared. This allows a user (e.g., surgeon or physician) to selectively shear only part of the tissue located adjacent first tubular member 120, thus potentially enabling the user to only shear tissue that is in a more concentrated field of view.

Figure 5:
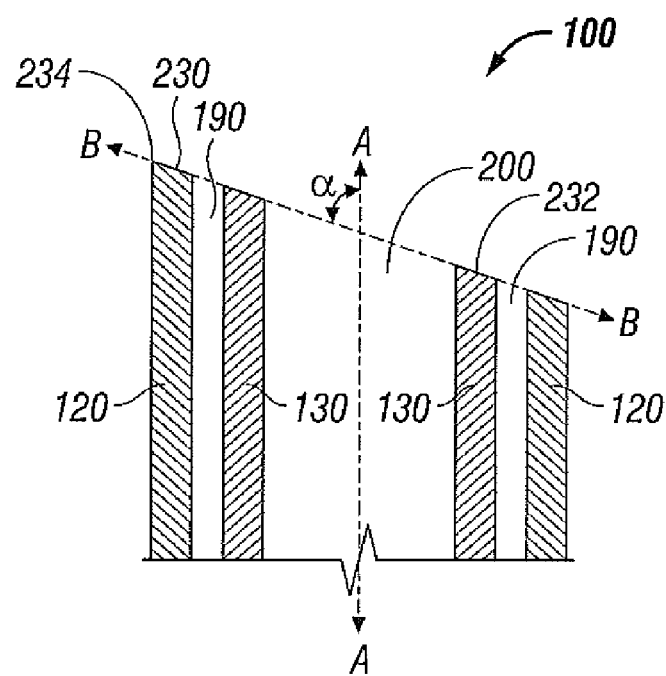
FIG. 5 is a cross-sectional view of a distal portion of the debrider apparatus of FIGS. 3 and 4.

The embodiment of debrider apparatus 100 illustrated in FIG. 5 shows first tubular member 120 and second tubular member 130 having angled distal surfaces 230, 232, respectively. Distal surfaces 230, 232 are defined by a second axis B-B that intersects first axis A-A at an acute angle α in this embodiment. Thus, distal surfaces 230, 232 are beveled at an angle relative to longitudinal axis A-A. Here, angle α may be in the range from about 10° to about 80°. Angled distal surfaces 230, 232 may enable the user to see a tip 234 of debrider instrument 100 more clearly, and thus enable the user to cut tissue more selectively. Additionally, angled distal surfaces 230, 232 of this embodiment may be used in conjunction with non-cutting zone 210 of FIGS. 3 and 4.

The present disclosure also relates to a method of shearing and coagulating/cauterizing tissue using a single instrument, e.g., debrider apparatus 100. In use, debrider apparatus 100 is provided and placed adjacent a tissue treatment area. Second tubular member 130 is moved (e.g., rotated or reciprocated) with respect to first tubular member 120, thus allowing debrider apparatus 100 to shear tissue disposed between first set of teeth 140 and second set of teeth 150. An electrical potential is supplied to at least one of first tubular member 120 and second tubular member 130, creating a potential difference therebetween. This bipolar quality enables debrider apparatus 100 to coagulate/cauterize tissue disposed adjacent the tissue treatment area.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended hereto.

What is claimed is:

1. A system for shearing and electrosurgically treating tissue, comprising:

a debrider apparatus including a first tubular member having a first set of teeth disposed circumferentially around about 25% to about 75% of a periphery of the first tubular member, the periphery adjacent a distal portion thereof, and a second tubular member having a second set of teeth disposed adjacent a distal portion thereof, the second tubular member at least partially disposed within the first tubular member and at least one of the first and the second tubular member being selectively movable relative to the other; and an electrosurgical generator that supplies the first tubular member with a first electrical potential and supplies the second tubular member with a second electrical potential, wherein the first tubular member includes a non-cutting zone disposed circumferentially around about 25% to about 75% of a periphery of the first tubular member.

2. The system of claim 1, further comprising at least one switch operably coupled to the debrider apparatus that both activates movement of one of the tubular members relative to the other of the tubular members and that controls the supply of electrical potentials to the first and second tubular members.

3. The system of claim 1, further comprising at least one lumen defined within at least one of the first tubular member and the second tubular member, the lumen configured to at least one of remove material from a tissue treatment site and supply a solution to the tissue treatment site.

4. A debrider apparatus, comprising:
a first tubular member including a distal portion, the first tubular member adapted to connect to a first potential of an electrosurgical generator;
a second tubular member including a distal portion, the second tubular member at least partially disposed within the first tubular member, the second tubular member being adapted to connect to a second potential of the electrosurgical generator, at least one of the first and the second tubular members being selectively movable relative to the other;
a first set of teeth disposed around about 25% to about 75% of a circumferential periphery of the first tubular member and adjacent the distal portion thereat the periphery of the first tubular member includes teeth and the remaining portion defines a non-cutting zone; and
a second set of teeth disposed around at least a portion of a periphery of the second tubular member and adjacent the distal portion thereof.

* * * * *